United States Patent
Suzuki et al.

(10) Patent No.: US 10,875,824 B2
(45) Date of Patent: Dec. 29, 2020

(54) NICKEL DIATOMACEOUS EARTH CATALYST AND METHOD FOR PRODUCING THE SAME

(71) Applicant: Mitsubishi Gas Chemical Company, Inc., Chiyoda-ku (JP)

(72) Inventors: Kouji Suzuki, Niigata (JP); Hajime Yamada, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/574,335

(22) Filed: Sep. 18, 2019

(65) Prior Publication Data

US 2020/0010404 A1    Jan. 9, 2020

Related U.S. Application Data

(62) Division of application No. 15/767,050, filed as application No. PCT/JP2016/082226 on Oct. 31, 2016, now abandoned.

(30) Foreign Application Priority Data

Nov. 2, 2015 (JP) .................................. 2015-215897

(51) Int. Cl.

| | | |
|---|---|---|
| B01J 23/755 | (2006.01) | |
| C07C 209/48 | (2006.01) | |
| B01J 37/03 | (2006.01) | |
| C07C 211/27 | (2006.01) | |
| B01J 35/10 | (2006.01) | |
| B01J 37/16 | (2006.01) | |
| B01J 35/00 | (2006.01) | |
| B01J 21/08 | (2006.01) | |
| B01J 37/02 | (2006.01) | |
| B01J 37/08 | (2006.01) | |
| B01J 37/18 | (2006.01) | |
| C07B 61/00 | (2006.01) | |

(52) U.S. Cl.
CPC ............ *C07C 209/48* (2013.01); *B01J 21/08* (2013.01); *B01J 23/755* (2013.01); *B01J 35/002* (2013.01); *B01J 35/006* (2013.01); *B01J 35/0046* (2013.01); *B01J 35/0053* (2013.01); *B01J 35/10* (2013.01); *B01J 35/1014* (2013.01); *B01J 35/1019* (2013.01); *B01J 37/0221* (2013.01); *B01J 37/0236* (2013.01); *B01J 37/03* (2013.01); *B01J 37/031* (2013.01); *B01J 37/038* (2013.01); *B01J 37/08* (2013.01); *B01J 37/16* (2013.01); *B01J 37/18* (2013.01); *C07C 211/27* (2013.01); *C07B 61/00* (2013.01)

(58) Field of Classification Search
CPC ....................................................... B01J 21/08
USPC .......................................................... 564/385
See application file for complete search history.

(56) References Cited

U.S. PATENT DOCUMENTS

| | | |
|---|---|---|
| 3,868,332 A | 2/1975 | Carter et al. |
| 5,498,587 A | 3/1996 | Deckers et al. |
| 5,600,030 A | 2/1997 | Deckers et al. |
| 2003/0013917 A1 | 1/2003 | Nakamura et al. |
| 2008/0009654 A1 | 1/2008 | Kumano et al. |

FOREIGN PATENT DOCUMENTS

| | | |
|---|---|---|
| CN | 101121665 A | 2/2008 |
| CN | 101491762 A | 7/2009 |
| JP | 48-22593 B | 7/1973 |
| JP | 50-1988 A | 1/1975 |
| JP | 63-145274 A | 6/1988 |
| JP | 4-372606 A | 12/1992 |
| JP | 5-239125 A | 9/1993 |
| JP | 7-821 A | 1/1995 |
| JP | 2001-98016 A | 4/2001 |
| JP | 2002-45694 A | 2/2002 |
| JP | 3265369 B2 | 3/2002 |
| JP | 2003-26639 A | 1/2003 |
| JP | 2012-30169 A | 2/2012 |
| RO | 91639 * | 5/1985 |

OTHER PUBLICATIONS

Johan Lif, et al., "Sintering of nickel particles supported on γ-alumina in ammonia," Applied Catalysis A: General, vol. 228, Issues 1-2, 2002, pp. 145-154.
International Search Report dated Nov. 29, 2016 in PCT/JP2016/082226 filed Oct. 31, 2016.
Salim et al., "Preparation of Catalysts VI," *Elsevier Science, B.V.*, pp. 1017-1026 (1995).
Tanaka, et al., "Kotai Hyoumen Characterization no Jissai", Feb. 10, 2005, pp. 142-145, with partial English translation, 5 pages.
Shogo Tawada, "Analysis of Temperature Programmed Desorption and Temperature Programmed Reaction Spectrum", J. Jpn. Soc. Colour Mater., 86 [1], pp. 20-25 (2013), with partial English translation, 7 pages.

\* cited by examiner

*Primary Examiner* — Ana Z Muresan

(74) *Attorney, Agent, or Firm* — Oblon, McClelland, Maier & Neustadt, L.L.P.

(57) ABSTRACT

A nickel diatomaceous earth catalyst having a weight loss rate measured by hydrogen-TG at 400 to 600° C. of 0.05 to 2.0%.

13 Claims, No Drawings

NICKEL DIATOMACEOUS EARTH CATALYST AND METHOD FOR PRODUCING THE SAME

TECHNICAL FIELD

The present invention relates to a nickel diatomaceous earth catalyst and a method for producing the same.

BACKGROUND ART

Hydrogenation reaction using an ammonia solvent has been widely conducted and a typical example thereof may include synthesis of amines from nitriles. While nickel, cobalt, platinum, palladium, rhodium and the like are used as a catalyst for the hydrogenation reaction, nickel is widely used in terms of cost and hydrogenation performance.

Common methods for producing a nickel catalyst include, for example, an impregnation method in which pores of a molding support are impregnated with a nickel-containing solution, which is fixed to pore walls and then dried and calcined to support active components, and a precipitation method in which precipitates of hydroxide, carbonate or the like are generated by bringing an aqueous solution of a nickel component in contact with a precipitant solution, which is then filtered, washed with water, dried, molded, and calcined. The precipitation method is suitable for preparing a multicomponent catalyst or a catalyst having a high supported ratio (20 to 40 wt %).

In the precipitation method, which is one of the methods for producing the nickel catalyst, essential characteristics of the catalyst are determined at a stage where precipitation reaction occurs, and an activation process after that stage is a stage for the catalyst to effectively exhibit its characteristics. Thus, it is difficult to modify catalytic performance after the precipitation reaction stage.

Catalytic activity and selectivity gradually decrease with use of the catalyst, which results in deterioration of catalytic activity. One of the causes for this activity deterioration is catalytic sintering. A sintering rate depends on an amount of supported metals, a size of metallic particles, a kind of a support, a reaction condition, and the like. As for the case of a metallic catalyst in general, it is effective to use a method in which crystallites of catalytic activity components are supported on a support having high heat resistance in a highly dispersed manner.

It has been known that heat resistance of the nickel catalyst in liquid ammonia and under a hydrogen atmosphere is low. Non-Patent Literature 1, for example, describes the heat resistance of the nickel catalyst supported on γ-alumina in the liquid ammonia and under the hydrogen atmosphere. It is stated that when the nickel catalyst is heat-treated at 110° C. to 150° C., no sintering occurs under the hydrogen atmosphere alone or under the ammonia atmosphere alone, but the sintering occurs when both hydrogen and ammonia are present simultaneously.

As a conventional precipitation method, Patent Literature 1, for example, describes a method in which a precursor produced by precipitating a compound containing nickel hydroxide and nickel carbonate on the surface of the support using the precipitation method is heat-treated with steam to produce a nickel catalyst excellent in both hydrogenation activity and heat resistance.

CITATION LIST

Patent Literature

Patent Literature 1: Japanese Patent Laid-Open No. 2012-30169

Non-Patent Literature

Non-Patent Literature 1: Johan Lif, Magnus Skoglundh, Lars Lowendahl. "Sintering of nickel particles supported on γ-alumina in ammonia", Applied Catalysis A: General, Volume 228, Issues 1-2, 2002, P. 145-154

SUMMARY OF INVENTION

Technical Problem

Although the method described in Patent Literature 1 is effective for preventing a decrease in a surface area when the catalyst is heated at 800° C., it is uncertain whether or not the method is effective in improving the heat resistance of the catalyst in the liquid ammonia and under the hydrogen atmosphere.

An object of the present invention is to provide a nickel diatomaceous earth catalyst having excellent heat resistance during hydrogenation reaction using an ammonia solvent, and a method for producing such a nickel diatomaceous earth catalyst.

Solution to Problem

The present inventors have conducted an extensive research to achieve the above-mentioned object and made the following findings to solve the problem.

That is, the present invention is as follows.

[1]

A nickel diatomaceous earth catalyst having a weight loss rate measured by hydrogen-TG at 400 to 600° C. of 0.05 to 2.0%.

[2]

The nickel diatomaceous earth catalyst according to the above [1], wherein a nickel crystallite diameter is 30 to 100 Å.

[3]

The nickel diatomaceous earth catalyst according to the above [1] or [2], wherein a change Δ in the nickel crystallite diameter between before and after a heat resistance test is 210 Å or less.

[4]

The nickel diatomaceous earth catalyst according to any of the above [1] to [3], wherein the nickel diatomaceous earth catalyst has a specific surface area of 60 to 180 m²/g.

[5]

A method for producing a nickel diatomaceous earth catalyst using a precipitation method, wherein the method comprises the steps of:

adding an alkaline solution as a precipitant to a dispersion liquid in which diatomaceous earth and a salt of a nickel catalyst are mixed; and performing a drying treatment, a calcination treatment, and a reduction treatment, in this order, wherein the reduction treatment is performed at a peak temperature +40° C. or more of a hydrogen-TPR measurement on a calcined powder produced by the calcination treatment.

[6]
The method for producing a nickel diatomaceous earth catalyst according to the above [5], wherein the reduction treatment is performed at the peak temperature +200° C. or less of the hydrogen-TPR measurement on the calcined powder produced by the calcination treatment.
[7]
A nickel diatomaceous earth catalyst produced by the method according to the above [5] or [6].
[8]
A method for producing xylylenediamine,
wherein the method comprises hydrogenating phthalonitrile in an ammonia solvent by using the nickel diatomaceous earth catalyst according to any of the above [1] to [4] and [7].

Advantageous Effects of Invention

The nickel diatomaceous earth catalyst of the present invention exhibits excellent heat resistance during the reaction with the liquid ammonia and under the hydrogen atmosphere. Accordingly, the catalyst can be used for the reaction at high temperatures, which can extend a life of the catalyst.

DESCRIPTION OF EMBODIMENTS

Hereinafter, a mode for carrying out the present invention (hereinafter, referred to as "the present embodiment") is described in detail. The present embodiment mentioned below is only an example for describing the present invention and is not intended to limit the present invention to the following descriptions. The present invention can be carried out by making modifications as appropriate within the outlined range.

In the present embodiment, each physical property can be measured in accordance with the method described in Examples below.
[Catalyst]
A nickel diatomaceous earth catalyst according to the present embodiment has a weight loss rate measured by hydrogen-TG at 400 to 600° C. of 0.05 to 2.0%. The weight loss rate measured by hydrogen-TG at 400 to 600° C. is preferably 0.1 to 1.8%, more preferably 0.1 to 1.0%. When the weight loss rate measured by hydrogen-TG at 400 to 600° C. is less than 0.05%, reduction needs to be carried out under severe conditions, which is disadvantageous in terms of cost efficiency and safety. The weight loss rate of more than 2.0%, on the other hand, provides the catalyst with poor heat resistance.

A specific surface area of the nickel diatomaceous earth catalyst according to the present embodiment is preferably 50 to 180 $m^2/g$, more preferably 60 to 180 $m^2/g$, further preferably 60 to 170 $m^2/g$. When the specific surface area of the catalyst is 50 $m^2/g$ or more, the catalyst tends to exhibit excellent hydrogenation performance. When the specific surface area is 180 $m^2/g$ or less, the catalyst tends to have excellent heat resistance.

A nickel crystallite diameter of the nickel diatomaceous earth catalyst according to the present embodiment is preferably 20 to 250 Å, more preferably 30 to 100 Å, further preferably 30 to 80 Å. When the nickel crystallite diameter of the catalyst is 20 Å or more, the heat resistance in liquid ammonia and under a hydrogen atmosphere tends to be improved. When the nickel crystallite diameter is 250 Å or less, the hydrogenation performance tends to be improved.

A change Δ in the nickel crystallite diameter between before and after a heat resistance test of the nickel diatomaceous earth catalyst according to the present embodiment is preferably 210 Å or less, more preferably 160 Å or less, further preferably 100 Å or less, in terms of the heat resistance.

The heat resistance test mentioned above refers to the heat resistance test described in Examples below.

The nickel diatomaceous earth catalyst according to the present embodiment may contain one or more components selected from the group consisting of Li, Na, K, Rb, Cs, Be, Ca, Sr, Ba, Ti, Cu, Cr, Zn, Mn, Mg, Ga, Ge, Nb, Ir, Pt, Bi, Al, In, Sr, Ce, Co, and Mo.
[Production Method]
A method for producing a nickel diatomaceous earth catalyst according to the present embodiment uses a precipitation method, the method including the steps of:
adding an alkaline solution as a precipitant to a dispersion liquid in which diatomaceous earth and a salt of a nickel catalyst are mixed; and
performing a drying treatment, a calcination treatment, and a reduction treatment. The reduction treatment is performed at a peak temperature +40° C. or more of a hydrogen-TPR measurement on a calcined powder produced by the calcination treatment.

The precipitation method is not limited to a particular method as long as a compound containing nickel hydroxide and nickel carbonate is deposited on a surface of the diatomaceous earth, and any of the conventionally known methods can be employed.
[Precipitation Treatment]
When preparing the dispersion liquid in which the diatomaceous earth and the salt of a nickel catalyst are mixed, the diatomaceous earth may be added to the solvent or the solvent may be added to the diatomaceous earth. When adding one to another, for example, the diatomaceous earth may be added to the solvent at 0 to 40° C., which is stirred for 30 to 60 minutes and then heated to a predetermined temperature, or the diatomaceous earth may be added to the solvent which has been heated to the predetermined temperature.

The salt of a nickel catalyst is not limited to a particular salt and examples thereof include nickel sulfate and nickel nitrate.

The alkaline solution as a precipitant is not limited to the particular one and examples thereof include an alkaline solution in which a carbonate such as sodium carbonate or sodium bicarbonate is dissolved. Into a dispersion liquid produced by adding a solution of a salt of the nickel catalyst to a solution in which the diatomaceous earth is dispersed, the alkaline solution as a precipitant may be poured using a tube pump or the like.

Pouring of the alkaline solution as a precipitant may be performed by either a regular pouring or a reverse pouring, but generally the method in which the alkaline solution as a precipitant is poured into the solution of a salt of a nickel catalyst (regular pouring method) is used. When the nickel catalyst is used, a precursor having a compound containing nickel hydroxide and nickel carbonate deposited on the surface of the diatomaceous earth can be produced. When a nickel source is nickel nitrate and an alkali source is sodium carbonate, the precipitation reaction is represented by the following formula (1), and as a result of the reaction, basic nickel carbonate is produced.

(Formula 1)

$$Ni(NO_3)_2 + Na_2CO_3 \rightarrow mNi(OH)_2 \cdot NiCO_3 + NaNO_3 \quad (1)$$

A molar ratio of alkali to nickel is preferably 1 to 4, more preferably 1.5 to 3. When the molar ratio of alkali to nickel falls within the above range, a precipitation pH is approximately 8 to 9. Accordingly, precipitation and deposition on the diatomaceous earth of basic nickel carbonate are more likely to occur.

When the alkaline solution as a precipitant is poured into the dispersion liquid of a catalyst component-containing solution in which the diatomaceous earth and the salt of a nickel catalyst are dissolved (hereinafter, referred to as "mother liquid"), the mother liquid is preferably maintained at 50 to 90° C., more preferably 60 to 80° C. Generating precipitates at a time of heating the mother liquid is more likely to make a particle diameter of precipitated particles uniform.

When a precipitation temperature is low, precipitated particles are generated slowly, and thus highly active catalytic precipitates are more likely to be produced. When the precipitation temperature is high, precipitates are produced in a short time, which can shorten a production process and also precipitated particles with small and even size can be produced.

When pouring the alkaline solution as a precipitant, it is preferable that the mother liquid is stirred. As a surface of generated precipitated particles has an agglomeration force acting among particles, stirring of the mother liquid can prevent an aggregate from growing large.

A length of time for pouring the precipitant is preferably 30 to 120 minutes, more preferably 60 to 90 minutes. It is preferable that heating and stirring are performed for a while after pouring so that aging of the precipitates proceeds. Changing an aging temperature can change the catalytic performance. The aging temperature may be either higher or lower than a pouring temperature and is preferably 50 to 90° C., more preferably 60 to 80° C., from the viewpoint of producing basic nickel carbonate from a generated precipitated component. An aging time is preferably about 0 to 3 hours, more preferably 0.5 to 2 hours, in terms of a time for basic nickel carbonate to be deposited and fixed on the diatomaceous earth.

As for the diatomaceous earth, a calcined product or a non-calcined product may be used. These products may be used singly or mixed together to achieve predetermined physical properties. However, with the calcined product alone, basic nickel carbonate is less likely to be deposited on the diatomaceous earth, which is more likely to end up producing a readily reducible catalyst. With the non-calcined product alone, basic nickel carbonate is readily deposited on the diatomaceous earth, which is more likely to end up producing a hardly reducible catalyst. When an appropriate reducibility is determined, an amount of basic nickel carbonate deposited on the diatomaceous earth is estimated from an amount of Si eluted in the treatment by the alkaline solution as a precipitant. An appropriate compounding ratio is determined by using the calcined product or the non-calcined product alone, or a mixture of both products.

For example, the amount of Si eluted when the diatomaceous earth is stirred at 80° C. for 2 hours using a 10% $Na_2CO_3$ aqueous solution is preferably 0.5 to 1.5%, more preferably 0.7 to 1.1%. When mixing the diatomaceous earth, the $Na_2CO_3$ aqueous solution may be added after the calcined product and the non-calcined product are mixed, or the calcined product and the non-calcined product of the diatomaceous earth may be separately added to the solution. As conditions for mixing, for example, the diatomaceous earth may be added to the solution of 10 to 40° C., which is stirred for 30 to 60 minutes and then heated to a predetermined temperature, or the diatomaceous earth may be added to the solution which has been heated to the predetermined temperature.

When the diatomaceous earth is used alone, changing an aging time depending on a kind of the diatomaceous earth can control the reducibility. For example, when the calcined product is used, a longer aging time is recommended as it is more likely to provide a readily reducible product. When the non-calcined product is used, a shorter aging time is recommended as it is more likely to provide a hardly reducible product.

Further, changing the aging temperature can also control the reducibility. For example, when the calcined product is used, a higher aging temperature is recommended as it is more likely to provide a readily reducible product. When the non-calcined product is used, a lower aging temperature is recommended as it is more likely to provide a hardly reducible product.

[Washing, Filtration, and Drying Treatment]

The precipitates produced by the precipitation treatment may be subjected to washing, filtration, and drying by a commonly used method. For example, the precipitates can be collected using Nutsche and further washed with water or the like to eliminate impurity ions (such as $SO_4^{2-}$ and $NO_3^-$). A nickel compound is easily bonded to S and N, and thus is hazardous as such bonding may produce a causative substance of poisoning. As for washing, a filtered cake once produced by the filtration is suspended in water and stirred to wash in suspension. The electrical conductivity of filtrate after washing in suspension is preferably set at 1 mS/cm or less. The filtered cake after being washed is fully dried at around 100° C. to produce a dried cake.

[Calcination Treatment]

The dried cake may be calcined by a commonly used method. For example, the calcination treatment is performed using an electric furnace. A calcination atmosphere may be provided with air or nitrogen. A calcination temperature is preferably 200 to 500° C., more preferably 350 to 450° C., in terms of the temperature at which nickel hydroxide or nickel carbonate is decomposed. A calcination time is preferably 3 to 10 hours, more preferably 5 to 7 hours, in terms of a time required to fully decompose nickel hydroxide or nickel carbonate. When the calcination treatment is performed on basic nickel carbonate, thermal decomposition is occurred as represented by the following formula (2), and nickel oxide (calcined powder) is produced.

(Formula 2)

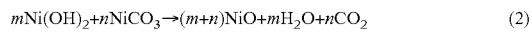

$$mNi(OH)_2 + nNiCO_3 \rightarrow (m+n)NiO + mH_2O + nCO_2 \qquad (2)$$

The catalyst reducibility is studied by performing temperature-programmed reduction with hydrogen (hydrogen-TPR measurement) on the calcined powder. A peak temperature of the hydrogen-TPR measurement is preferably 200 to 500° C., more preferably 300 to 400° C., further preferably 300 to 360° C. The nickel catalyst prepared by the above method is in a state of an oxidative product and exhibits no catalytic activity in that state.

[Reduction Treatment]

After the calcination treatment, the reduction treatment is performed to activate the catalyst (refer to the following formula (3)). As a reductant used in this case, commonly used reductants such as hydrogen, carbon monoxide, and methanol may be used. Hydrogen is preferably used in terms of toxicity and easy handling. For example, a certain amount of the catalyst after calcination is placed in a reaction tube made of SUS, which is heated under a nitrogen atmosphere, and hydrogen gas is introduced into the reaction tube. The reaction temperature is preferably 350 to 500° C., more preferably 380 to 450° C.

Although an amount of an unreduced nickel compound can be reduced by performing the reduction reaction at a higher temperature, a specific surface area becomes small and activity tends to deteriorate when the temperature is too high. Additionally, raising the temperature requires time and energy, and thus is not cost-effective and also increases a risk.

(Formula 3)

$$NiO + H_2 \rightarrow Ni + H_2O \qquad (3)$$

The acceleration of sintering is attributed to the nickel compound remaining unreduced (unreduced nickel compound). To perform reduction in such a manner that less unreduced nickel compounds are produced, a reduction treatment temperature is set higher than a peak temperature of the temperature-programmed reduction with hydrogen (hydrogen-TPR measurement) performed on the calcined powder produced by the calcination treatment. More specifically, the reduction treatment temperature is performed at a peak temperature +40° C. or more, preferably at a peak temperature +50° C. or more, more preferably at a peak temperature +60° C. or more, of the hydrogen-TPR measurement on the calcined powder. An upper limit of the reduction treatment temperature is not limited to a particular temperature and is performed preferably at a peak temperature +200° C. or less, more preferably at a peak temperature +150° C. or less, further preferably at a peak temperature +100° C. or less, of the hydrogen-TPR measurement on the calcined powder, from the viewpoint of preventing a decrease in the catalytic activity.

After the reduction reaction, the nickel catalyst is cooled down to room temperature under a nitrogen atmosphere and stabilized. When the activated nickel catalyst is exposed to air, it causes sudden oxidative heat generation which leads to deterioration of the activity. For that reason, it is necessary to pay a careful attention not to expose the catalyst to the outside air and also necessary to pay a careful attention to a preserving period when keeping and handling the catalyst. To maintain the catalytic performance, a surface of the reduced nickel is subjected to partial oxidization at a low temperature or adsorption with inert gas such as carbon dioxide and nitrogen to protect the surface, or, depending on applications, the catalyst is dispersed in a solvent such as oil for protection of the surface.

One or more components selected from the group consisting of Li, Na, K, Rb, Cs, Be, Ca, Sr, Ba, Ti, Cu, Cr, Zn, Mn, Mg, Ga, Ge, Nb, Ir, Pt, Bi, Al, In, Sr, Ce, Co, and Mo can be added to the catalyst as necessary. As a method for adding the components, aqueous solutions of each component and a nickel salt solution may be mixed first and a precipitant may be poured into the mixture to produce the precipitates, or a certain amount of compounds of each component may be added to the precipitates produced by the washing and filtration treatment.

A shape of the catalyst is not limited to a particular shape and may be molded into a required shape and size according to the condition of use. For example, when high mechanical strength is required for catalyst particles or when sufficient strength cannot be gained by other molding methods, a compression molding method can be used. In the compression molding method, for example, graphite may be added to mold the catalyst into the form of pellet by means of tablet molding. When high mechanical strength is not required, an extrusion molding method which is excellent in productivity and continuous production can be used. When this method is used, an inorganic binder may be added as a strength improver. Examples of the inorganic binder include clay minerals such as kaolin and montmallonite; silica sol; and alumina sol. A particle diameter of the nickel catalyst after the molding process is preferably about 0.1 mm to 10 mm.

The nickel diatomaceous earth catalyst according to the present embodiment can be used for all hydrogenation reactions in an ammonia solvent. For example, by hydrogenating phthalonitrile, isophthalonitrile (IPN), terephthalonitrile (TPN), or a mixture of isophthalonitrile and terephthalonitrile (IPN/TPN) in the ammonia solvent, xylylenediamine, meta-xylylenediamine (MXDA), para-xylylenediamine (PXDA), of a mixture of meta-xylylenediamine and para-xylylenediamine (MXDA/PXDA) can be produced.

EXAMPLES

Hereinafter, the present embodiment is described in detail with reference to the following Examples. However, the present embodiment is not limited only to the following Examples.

Measurement methods and evaluation methods for each physical property in Examples and Comparative Examples are as follows.

[Measurement of Physical Properties]

Physical properties of the dried cake were measured. The dried cake was pounded in a mortar and subsequently filtered through a 60 to 80 mesh screen to produce a dried powder, which was used as a measurement sample. As to the measurement of a specific surface area, a specific surface area analyzer (NOVA 4200e manufactured by Quantachrome Instruments) was used. After the measurement sample was pretreated by drying at 100° C. for 5 hours, the specific surface area was measured by a nitrogen adsorption measurement (BET method).

Next, physical properties of calcined powder were measured. A specific surface area was measured in the same manner as described above.

A nickel metal surface area was calculated by measuring an amount of hydrogen adsorption of a reduced catalyst using a method described below. BELCAT-B (manufactured by BEL Japan, Inc.) was used as a measuring device. First, about 0.4 g of the calcined powder was placed in a U-shaped glass tube. Into the reaction tube with an inner temperature being set at 340° C., helium (50 mL/min) was introduced for 45 minutes followed by hydrogen (50 mL/min) for 30 minutes to reduce the catalyst with hydrogen. Next, while keeping the reduced catalyst in the U-shaped glass tube, helium (50 mL/min) was introduced thereinto for 10 minutes and left to cool down to room temperature. After that, while keeping the reduced catalyst in the U-shaped glass tube, hydrogen gas (50 mL/min) was repeatedly introduced for 1 minute and a hydrogen concentration of discharged gas was measured by gas chromatography. The hydrogen gas was pulsed until there was no increase or decrease in the hydrogen concentration at the inlet and outlet of the U-shaped tube, and the nickel metal surface area was calculated based on the amount of adsorption.

Reduction behavior was measured by the hydrogen-TPR. BELCAT-A (manufactured by BEL Japan, Inc.) was used as a measuring device. 0.1 g of the calcined powder was placed in the reaction tube, an inner temperature of the tube was set at 200° C., and then helium (50 mL/min) was introduced thereinto for 30 minutes. After that, the flowing gas was switched to 10% hydrogen/90% argon (50 mL/min) and heated to 800° C. at a heating rate of 2° C./min, and the reducibility at this time was measured from a hydrogen consumption to calculate a peak temperature of the hydrogen-TPR.

Next, physical properties of a reduced and stabilized product were measured. The product was pounded in a mortar and subsequently filtered through a 60 to 80 mesh screen to produce a powder, which was used as a measurement sample.

A specific surface area was measured in the same manner as described above.

The reduction behavior was measured by thermogravimetry (TG). A differential thermogravimetric analyzer (Thermo plus evo TG8120 manufactured by Rigaku Corporation) was used as a measuring device. About 10 mg of the reduced and stabilized product was put into the device and 3% hydrogen/97% nitrogen (50 mL/min) was introduced. The temperature was raised to 600° C. at the heating rate of 10° C./min, and a weight loss rate at a high temperature range of 400 to 600° C. was measured at this time. The weight loss rate is considered to indicate desorption of the oxygenated compound from the unreduced nickel and is a reference index indicating an amount of the unreduced nickel.

[Heat Resistance Test]

Heat resistance of the catalyst in liquid ammonia and under a hydrogen atmosphere was evaluated. After 0.4 g of the reduced and stabilized product (60 to 80 mesh) was placed in a reaction tube made of SUS having an inner diameter of 6 mm, an inner temperature of the reaction tube was set at 250° C. and hydrogen (40 mL/min) was introduced thereinto for 10 hours to produce a reduced catalyst. After that, in the reaction tube, an inner pressure was set at hydrogen 10 MPaG, the inner temperature was set at 120° C., and the liquid ammonia (10 g/h) and hydrogen (40 mL/min) were introduced thereinto for 14 hours. After the liquid ammonia was introduced, the temperature and the pressure in the reaction tube were brought back to normal, and then the catalyst was taken out to measure a nickel crystallite diameter by an XRD device (MiniFlex600 manufactured by Rigaku Corporation).

[Activity Test]

3% by mass of graphite was added to the calcined powder, which was then molded into 6 mmq×6 mm by a tablet molding machine, and a reduced and stabilized product was produced in the same manner as described above. An activity (hydrogenation reaction) test was conducted as follows using the aforementioned reduced and stabilized product. In a 100 mL autoclave reaction vessel made of SUS, 2 g of the reduced and stabilized product was placed, and then an inner temperature of a reaction tube was set at 250° C. and 50% hydrogen/50% nitrogen was introduced at 20 mL/min for 10 hours. Subsequently, the reaction vessel was filled with 10 g of meta-xylene (manufactured by Wako Pure Chemical Industries, Ltd.), 6.7 g of isophthalonitrile (manufactured by Tokyo Chemical Industry Co., Ltd.), and 10 g of the liquid ammonia, and hydrogen was filled up to 10 MPaG. After hydrogen was filled, a resultant in the vessel was heated at 80° C. for 2 hours with stirring to allow the hydrogenation reaction to proceed in the vessel to produce meta-xylenediamine (MXDA).

[Amount of Si Eluted of Diatomaceous Earth]

80 mL of a 10% $Na_2CO_3$ aqueous solution was added to 2 g of the diatomaceous earth, which was stirred at 60° C. for 2 hours. The amount of Si eluted contained in a resultant solution was measured by ICP-AES (Vista manufactured by Varian Inc.). Results are shown in Table 1.

In Table 2, an average amount of Si eluted of the diatomaceous earth used in each Example and Comparative Example was shown.

TABLE 1

| Diatomaceous earth | Kind | Amount (%) of Si eluted |
|---|---|---|
| Celite 503 | Calcined product | 0.28 |
| Diaful #110 | Non-calcined product | 1.2 |
| Filter cell | Non-calcined product | 1.9 |

Example 1

In a 3 L three-neck flask, 17.5 g of filter cell (non-calcined product, manufactured by Imerys S.A.) and 17.5 g of celite 503 (calcined product, manufactured by Imerys S.A.) as diatomaceous earth, 283.2 g of nickel sulfate hexahydrate (manufactured by Wako Pure Chemical Industries, Ltd.) as a nickel source, and 1000 g of water were mixed at 25° C. to prepare slurry. Slurry was stirred at 300 rpm and heated to 70° C.

In another vessel, 202 g of sodium carbonate (manufactured by Wako Pure Chemical Industries, Ltd.) was dissolved in 1000 g of water to prepare a precipitant. With a tube pump, the precipitant was poured into slurry at 20 g/min. While pouring, slurry was maintained at a temperature of 70° C. and stirred. After the whole quantity of the precipitant was poured, a resultant was heated to 80° C. at 2° C./min and stirred for 2 hours to allow aging to proceed. After that, the produced slurry was subjected to filtration under a reduced pressure using Nutsche (filter paper: Advantec 4A) to produce a filtered cake.

In a 3 L jug made of polypropylene, the filtered cake was placed and 1000 g of pure water was added with stirring at 25° C. to transform the filtered cake into slurry again, which was then washed in suspension and filtered. Washing in suspension and filtration were performed repeatedly until the electrical conductivity of filtrate reached 0.5 mS/cm or less. The filtered cake was dried at 110° C. for 12 hours using an electric dryer to produce a dried cake.

The dried cake was calcined at 380° C. for 5 hours in a calcination furnace to produce a catalyst calcined cake. This calcined cake was pulverized to produce a catalyst calcined powder.

The catalyst calcined powder was placed in a reaction tube made of SUS having an inner diameter of 1.4 cm and reduction was performed at 400° C. for 10 hours using 50% hydrogen/50% nitrogen gas (60 mL/min). After the reduction was stabilized, the reduced product was left to cool down to room temperature under the nitrogen atmosphere, and 1% oxygen/99% nitrogen gas (60 mL/min) was circulated for 4 hours and 40 oxygen/96% nitrogen gas (60 mL/min) was subsequently circulated for 2 hours for stabilization to produce a reduced and stabilized product. Measurement results are shown in Table 2.

A crystallite diameter of nickel before and after the test changed from 42 Å to 180 Å. A nickel crystallite after the test was 180 Å with a small crystallite growth and high heat resistance.

Example 2

A nickel diatomaceous earth catalyst was produced in the same manner as in Example 1 except that the reduction conditions of the catalyst calcined powder were changed to 450° C. and 10 hours. Measurement results are shown in Table 2.

Example 3

A nickel diatomaceous earth catalyst was produced in the same manner as in Example 1 except that the reduction conditions of the catalyst calcined powder were changed to 380° C. and 10 hours. Measurement results are shown in Table 2.

Comparative Example 1

A nickel diatomaceous earth catalyst was produced in the same manner as in Example 1 except that the reduction conditions of the catalyst calcined powder were changed to 310° C. and 10 hours. Measurement results are shown in Table 2.

Example 4

A nickel diatomaceous earth catalyst was produced in the same manner as in Example 1 except that the ratio of the filter cell/celite 503 in the diatomaceous earth was changed to 25% by mass/75% by mass. Measurement results are shown in Table 2.

Example 5

A nickel diatomaceous earth catalyst was produced in the same manner as in Example 1 except that the ratio of the filter cell/celite 503 in the diatomaceous earth was changed to 75% by mass/25% by mass. Measurement results are shown in Table 2.

Comparative Example 2

A nickel diatomaceous earth catalyst was produced in the same manner as in Example 1 except that the ratio of the filter cell in the diatomaceous earth was changed to 100% by mass and the aging time was changed to 180 minutes. Measurement results are shown in Table 2.

Comparative Example 3

A nickel diatomaceous earth catalyst was produced in the same manner as in Example 1 except that the ratio of the filter cell/Diafil #110 (non-calcined product, manufactured by Imerys S.A.) in the diatomaceous earth was changed to 50% by mass/50% by mass and the aging time was changed to 180 minutes. Measurement results are shown in Table 2.

Example 6

A nickel diatomaceous earth catalyst was produced in the same manner as in Example 2 except that the aging time was changed to 100 minutes. Measurement results are shown in Table 2.

Example 7

A nickel diatomaceous earth catalyst was produced in the same manner as in Example 2 except that the aging temperature was changed to 70° C. and the aging time was changed to 120 minutes. Measurement results are shown in Table 2.

Example 8

A nickel diatomaceous earth catalyst was produced in the same manner as in Example 2 except that the ratio of celite 503 in the diatomaceous earth was changed to 100% by mass. Measurement results are shown in Table 2.

Example 9

A nickel diatomaceous earth catalyst was produced in the same manner as in Comparative Example 2 except that the reduction temperature was changed to 420° C. Measurement results are shown in Table 2.

Example 10

A nickel diatomaceous earth catalyst was produced in the same manner as in Comparative Example 3 except that the reduction temperature was changed to 420° C. Measurement results are shown in Table 2.

Example 11

A nickel diatomaceous earth catalyst was produced in the same manner as in Comparative Example 2 except that the reduction temperature was changed to 450° C. Measurement results are shown in Table 2.

Example 12

A nickel diatomaceous earth catalyst was produced in the same manner as in Comparative Example 3 except that the reduction temperature was changed to 450° C. Measurement results are shown in Table 2.

TABLE 2

| | Support | Amount of Si eluted % | Aging temperature ° C. | Aging time min | Dried powder Specific surface area $m^2/g$ | Calcined powder Specific surface area $m^2/g$ | Surface area of Ni $m^2/g$ | Peak temperature of $H_2$-TPR (T) ° C. |
|---|---|---|---|---|---|---|---|---|
| Example 1 | Filter cell/Celite 503 = 50/50 | 1.1 | 80 | 120 | 288 | 245 | 32 | 317 |
| Example 2 | Filter cell/Celite 503 = 50/50 | 1.1 | 80 | 120 | 288 | 245 | 32 | 317 |
| Example 3 | Filter cell/Celite 503 = 50/50 | 1.1 | 80 | 120 | 288 | 245 | 32 | 317 |
| Comparative Example 1 | Filter cell/Celite 503 = 50/50 | 1.1 | 80 | 120 | 288 | 245 | 32 | 317 |

TABLE 2-continued

| | | | | | | | | |
|---|---|---|---|---|---|---|---|---|
| Example 4 | Filter cell/Celite 503 = 25/75 | 0.7 | 80 | 120 | 252 | 191 | 23 | 324 |
| Example 5 | Filter cell/Celite 503 = 75/25 | 1.5 | 80 | 120 | 257 | 250 | 32 | 360 |
| Comparative Example 2 | Filter cell | 1.9 | 80 | 180 | 192 | 109 | 22 | 372 |
| Comparative Example 3 | Filter cell/ Diafil #100 = 50/50 | 1.6 | 80 | 180 | 195 | 112 | 24 | 375 |
| Example 6 | Filter cell | 1.9 | 80 | 100 | 251 | 194 | 35 | 315 |
| Example 7 | Filter cell | 1.9 | 70 | 120 | 255 | 198 | 37 | 311 |
| Example 8 | Celite 503 | 0.3 | 80 | 90 | 210 | 118 | 18 | 301 |
| Example 9 | Filter cell | 1.9 | 80 | 180 | 192 | 109 | 22 | 372 |
| Example 10 | Filter cell/ Diafil #100 = 50/50 | 1.6 | 80 | 180 | 195 | 112 | 24 | 375 |
| Example 11 | Filter cell | 1.9 | 80 | 180 | 192 | 109 | 22 | 372 |
| Example 12 | Filter cell/ Diafil #100 = 50/50 | 1.6 | 80 | 180 | 195 | 112 | 24 | 375 |

| | Reduced and stabilized product | | | Reduced and stabilized product Heat resistance test | | | |
|---|---|---|---|---|---|---|---|
| | Reduction temperature (T') °C. | T' − T °C. | Specific surface area $m^2/g$ | Weight loss measured by TG at 400-600° C. % | Crystallite diameter (before test) Å | Crystallite diameter (after test) Å | Δ Å | Activity test MXDA yield % |
| Example 1 | 400 | 83 | 119 | 0.55 | 42 | 180 | 138 | 26 |
| Example 2 | 450 | 133 | 105 | 0.1 | 60 | 100 | 40 | 22 |
| Example 3 | 380 | 63 | 122 | 1.8 | 40 | 250 | 210 | 28 |
| Comparative Example 1 | 310 | −7 | 189 | 4.0 | 25 | 390 | 365 | 9 |
| Example 4 | 400 | 76 | 105 | 0.41 | 73 | 121 | 48 | 20 |
| Example 5 | 400 | 40 | 125 | 1.4 | 40 | 230 | 190 | 27 |
| Comparative Example 2 | 400 | 28 | 68 | 3.1 | 105 | 342 | 237 | 15 |
| Comparative Example 3 | 400 | 25 | 65 | 3.0 | 102 | 349 | 247 | 26 |
| Example 6 | 400 | 85 | 118 | 1.2 | 35 | 185 | 150 | 27 |
| Example 7 | 400 | 89 | 123 | 1.2 | 38 | 179 | 141 | 26 |
| Example 8 | 400 | 99 | 71 | 0.33 | 100 | 136 | 36 | 12 |
| Example 9 | 420 | 48 | 67 | 1.8 | 107 | 259 | 152 | 16 |
| Example 10 | 420 | 45 | 64 | 1.9 | 105 | 261 | 156 | 27 |
| Example 11 | 450 | 78 | 65 | 0.8 | 110 | 225 | 115 | 14 |
| Example 12 | 450 | 75 | 63 | 0.9 | 109 | 227 | 118 | 25 |

In Example 1, the crystallite diameter after the heat resistance test of around 180 Å was achieved by making the weight loss rate measured by TG at 400 to 600° C. 0.55%.

In Example 2, the crystallite diameter after the heat resistance test of around 100 Å was achieved by making the weight loss rate measured by TG at 400 to 600° C. 0.1%, and sintering resistance was improved.

In Example 3, the crystallite diameter after the heat resistance test of around 250 Å was achieved by making the weight loss rate measured by TG at 400 to 600° C. 1.8%.

In Examples 3, 4, and 5, and Comparative Examples 2 and 3, changing ratio of the non-calcined product and the calcined product in the diatomaceous earth was able to make changes in the amount of Si eluted and the amount of weight loss measured by TG at 400 to 600° C. When the weight loss rate was above 2.0%, the crystallite diameter after the heat resistance test became more than 300 Å and the sintering resistance was reduced.

In Examples 6 and 7, even though the diatomaceous earth was composed of the non-calcined product only, the amount of weight loss measured by TG at 400 to 600° C. was able to be reduced by changing the aging time and aging temperature of the precipitation in Comparative Example 2, and the sintering resistance was improved.

In Examples 8 to 12, the heat resistance of the catalyst was good.

The present application is based on the Japanese patent application (Japanese Patent Application No. 2015-215897) filed with the Japan Patent Office on Nov. 2, 2015, and the content thereof is hereby incorporated for reference.

The invention claimed is:

1. A method for producing a nickel diatomaceous earth catalyst by a precipitation method, comprising:
   adding an alkaline solution as a precipitant to a dispersion liquid in which diatomaceous earth and a salt of a nickel catalyst are mixed; and
   performing a drying treatment, a calcination treatment, and a reduction treatment, in this order, to obtain the nickel diatomaceous earth catalyst,
   wherein the reduction treatment is performed at a temperature that is +40° C. or more and 200° C. or less of a peak temperature of a hydrogen-TPR measurement on a calcined powder produced by the calcination treatment and within a range of 380-450° C. to form a nickel diatomaceous earth catalyst having:
   a nickel crystallite diameter of 30 to 100 Å,
   a change Δ in the nickel crystallite diameter between before and after a heat resistance test of 210 Å or less, and
   a specific surface area of 60 to 180 $m^2/g$.

2. The method according to claim 1, wherein the reduction treatment is performed at the peak temperature +150° C. or less of the hydrogen-TPR measurement on the calcined powder produced by the calcination treatment.

3. The method according to claim 1, wherein the nickel diatomaceous earth catalyst has a weight loss rate measured by hydrogen-TG at 400 to 600° C. of 0.05 to 2.0%.

4. The method according to claim 1, wherein the salt of a nickel catalyst is selected from nickel sulfate and nickel nitrate.

5. The method according to claim 1, wherein the alkaline solution is poured into the dispersion liquid in which diatomaceous earth and the salt of a nickel catalyst are mixed to produce a precursor having a compound containing nickel hydroxide and nickel carbonate deposited on the surface of the diatomaceous earth.

6. The method according to claim 1, wherein the alkaline solution is added to the dispersion liquid while the dispersion liquid is maintained at a temperature of 50-90° C.

7. The method according to claim 1, further comprising: after the reduction treatment, contacting the nickel diatomaceous earth catalyst with carbon dioxide to at least partially oxidize nickel metal present thereon.

8. The method according to claim 1, wherein the diatomaceous earth comprises a calcined diatomaceous earth component and a non-calcined diatomaceous earth component.

9. The method according to claim 1, wherein the alkaline solution is an aqueous solution of sodium carbonate.

10. The method according to claim 1, further comprising: aging a mixture formed by adding the alkaline solution to the dispersion liquid for at least two hours before performing the drying treatment.

11. The method according to claim 1, wherein the reduction treatment comprises contacting a calcined product formed from the calcination treatment with a hydrogen-containing gas at a temperature of from 400 to 450° C. then contacting the calcined product with an oxygen-containing gas to produce a stabilized product.

12. The method according to claim 1, wherein the reduction treatment is performed at a peak temperature that is +40° C. or more and 100° C. or less of the peak temperature of a hydrogen-TPR measurement.

13. The method according to claim 1, wherein the reduction treatment is performed at a peak temperature that is 40° C. or more and 133° C. or less of the peak temperature of a hydrogen-TPR measurement and within a range of 380-450° C. to form a nickel diatomaceous earth catalyst having:
a nickel crystallite diameter of 30 to 100 Å,
a change Δ in the nickel crystallite diameter between before and after a heat resistance test of 210 Å or less, and
a specific surface area of 60 to 180 m$^2$/g.

\* \* \* \* \*